United States Patent [19]

Josten et al.

[11] 4,387,199
[45] Jun. 7, 1983

[54] TETRAVALENT VANADIUM COMPOUNDS WHICH ARE SOLUBLE IN ORGANIC SOLVENTS

[75] Inventors: Walter Josten, Rheinfelden; Hans-Joachim Vahlensieck, Wehr, both of Fed. Rep. of Germany

[73] Assignee: Dynamit Nobel Aktiengesellschaft, Cologne, Fed. Rep. of Germany

[21] Appl. No.: 310,161

[22] Filed: Oct. 9, 1981

Related U.S. Application Data

[62] Division of Ser. No. 179,586, Aug. 21, 1980, Pat. No. 4,324,736.

[30] Foreign Application Priority Data

Aug. 24, 1979 [DE] Fed. Rep. of Germany ....... 2934277

[51] Int. Cl.$^3$ .............................................. C08F 4/68
[52] U.S. Cl. .................................. 526/113; 526/116; 526/120; 526/121; 528/411
[58] Field of Search ............... 526/116, 113, 120, 121; 528/411

[56] References Cited

U.S. PATENT DOCUMENTS 3,062,803 11/1962 Farnham et al. ................. 526/169.2
3,294,766 12/1966 Henderson et al. .............. 526/169.2
3,567,653 3/1971 Wagensommer et al. .......... 526/116

Primary Examiner—Edward J. Smith
Attorney, Agent, or Firm—Sprung, Horn, Kramer & Woods

[57] ABSTRACT

A compound of tetravalent vanadium of the general formula

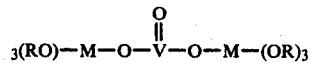

wherein M represents a metal of the fourth group of the Periodic Table of the Elements and R represents and alkyl, cycloalkyl or aryl moiety of 1 to 20 carbon atoms and a process for its preparation. Also disclosed is the use of such vanadium compound as a catalyst for homopolymerization, copolymerization or terpolymerization of various monomers including olefins and vinyl monomers.

8 Claims, No Drawings

TETRAVALENT VANADIUM COMPOUNDS WHICH ARE SOLUBLE IN ORGANIC SOLVENTS

This is a division of application Ser. No. 179,586, filed Aug. 21, 1980, now U.S. Pat. No. 4,324,736, Apr. 13, 1982.

BACKGROUND OF THE INVENTION

1. Field of the Invention

This invention relates to new vanadium (IV) alcoholates which are soluble in organic solvents and have greater stability than known vanadium alcoholates.

2. Discussion of Prior Art

Alcoholates of tetravalent vanadium, which are used, for examples, as polymerization catalysts, are already known. They correspond to the formula V(OR)$_4$ and they are soluble in some polar organic solvents. However, they are expensive and difficult to prepare, because they cannot be made by the direct reaction of VCl$_4$ with alcohols, because of the proneness of this compound to hydrolysis. Instead, VCl$_4$ has to be reacted with lithium dialkylamide and the tetrakis-(dialkylamino) vanadium (IV) thus obtained must be subjected to alcoholysis.

These known alcoholates of tetravalent vanadium also have the disadvantage that they are not thermostable. At temperatures above 100° C., they begin to decompose. Their shelf life also leaves much to be desired, and they can be stored satisfactorily only if certain precautionary rules are followed. Also the alcoholates of pentavalent vanadium, such as for example VO(OCH$_3$)$_3$ or VO(OC$_2$H$_5$)$_3$, which are also used as catalysts, have the same instability, so that they are not satisfactory replacements for the vanadium (IV) compounds.

SUMMARY OF THE INVENTION

The problem therefore existed of finding compounds of tetravalent vanadium which are easy to prepare, do not decompose at temperatures up to 150° C., have good shelf life, and are soluble in nonpolar organic solvents.

As a solution to this problem, di(trialkylate)-oxovanates (IV) have been found, which correspond to the formula:

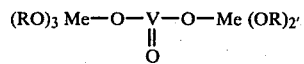

in which Me represents a metal of the fourth group of the Periodic Table of the Elements and R represents an alkyl moiety of 1 to 20 carbon atoms or an aryl moiety, i.e. aryl of 6-18 carbocyclic carbon atoms.

The new compounds are soluble in nonpolar organic solvents and do not decompose even at temperatures of 190° C. Their preparation is accomplished in a simple, known manner by the reaction of vanadyl carboxylates with alcoholates of titanium or zirconium or hafnium.

In the metal alcoholates that can be used as starting products for the preparation of the new alcoholates, the alcohol moiety can be either an aliphatic or cycloaliphatic or an aromatic moiety. The aliphatic moiety can be straight-chained or branched and can contain up to 20 carbon atoms. Particularly contemplated are aliphatic alcohols derived from aliphatic hydrocarbons, especially saturated hydrocarbons. Thus the alcohols can be alkanols, alkenols and alkynols as well as their cyclic counterparts. The aromatic moieties are mainly the phenyl and the cresyl moieties, although the aryl compound can have up to 18, preferably up to 12 moieties. Examples of compounds of this kind are methyl titanate, ethyl titanate, n-propyl titanate, isobutyl titanate, nonyl titanate, 2-ethylhexyl titanate, cetyl titanate, cresyl titanate, methyl zirconate, butyl zirconate, oleyl zirconate (IV), and phenyl zirconate (IV).

The preferred alkyl moieties of metallic acid esters are those having 1 to 10 carbon atoms.

These metallic acid esters are reacted with vanadyl carboxylates of the formula VO(OOCR')$_2$' wherein R' is an alkyl moiety of 1 to 5 carbon atoms, preferably the methyl moiety. The molar ratio of vanadyl carboxylate to metallic acid ester is preferably 1:1.8 to 2.2. In the reaction, a half ester of the vanadyl compound

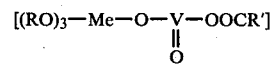

develops as an intermediate product, although it does not have to be isolated, and also the corresponding carboxylic acid ester.

The reaction can be performed in the absence of solvent, although it is recommendable to perform the reaction in a high-boiling solvent, such as toluene, xylene, cumene, tetrahydronaphthalene (Tetralin), decahydronaphthalene (Decalin) or aliphatic, high-boiling hydrocarbons. The half ester forms at temperatures between 100° and 150° C. Heating is continued further until the reaction is complete, the temperatures being able to be increased up to 200° C.

Generally the compounds of the invention are prepared by performing the reaction at 80° to 240° C., preferably 120° to 200° C. lower pressures down to 5 mbar and higher pressures up to 2,5 bar can be used within the given temperature ranges.

The carboxylic acid ester that develops in the reaction is continuously distilled out during the reaction provided that its boiling point is below the boiling point of the solvent used. The progress of the reaction can also be followed by measuring the amount of carboxylic acid ester that is distilled out.

After the reaction has ended, any remaining carboxylic acid ester is distilled out, and the new metallic acid ester obtained is freed of solvent and vacuum distilled if necessary.

The new metallic acid esters are soluble in nonpolar organic solvents and can accordingly be used as catalysts in solution. In addition, they are soluble in lower-boiling aromatic and nonpolar aliphatic solvents, such as for example benzene, hexane or benzine gasoline fractions. These solutions are stable for several months at room temperature if moisture is excluded.

The new compounds are suitable as catalysts in the polymerization of olefins and dienes and in the copolymerization thereof. Furthermore, they can also be used as catalysts in the polymerization of vinyl chloride, acrylic acid esters or epoxides, and in esterification or transesterification reactions. They can be used in the same manipulative manner and in the same amounts as known olefin and diene polymerization catalyst which contains vanadium. Similarly when employed for vinyl polymerization or polymerization of acrylic acid esters or epoxides, the new vanadium compounds are employed in the same manner and in the same amount as conventional catalysts therefor.

The new compounds can be used to form homopolymers, copolymers and terpolymers of the above named monomers.

EXAMPLES

Example 1

Preparation of di(tri-butyltitanate)-oxo-vanadate(IV) of the formula O=V—[O—Ti(O—C$_4$H$_9$)$_3$]$_2$.

6.46 kg of vanadium-oxo-acetate (96.7% pure) was suspended in 30 liters of a mixture of aliphatic hydrocarbons of a boiling range between 184° and 211° C. Then, with stirring, 23 kg of titanium tetrabutylate was slowly added, and then the mixture was heated. As soon as a temperature of 155° C. had been reached in the reaction mixture, the acetic acid butyl ester that formed during the reaction was distilled out through a short fractionating column. While this ester was being removed the internal temperature rose to 190° C.

Then the solvent was distilled out in a rotary evaporator at 1 to 10 mbar. A brownish-black, viscous liquid is obtained. Analysis shows a content of 16.3% titanium and 8.6% vanadium.

The new compound is miscible in n-hexane in all proportions. These solvents are stable for more than three months at room temperature, if moisture is excluded.

EXAMPLE 2

Preparation of di(triacetyltitanate)-oxo-vanadate(IV)

3.8 kg of vanadyl acetate was dissolved in a high-boiling, aliphatic hydrocarbon. 46.6 kg of cetyl titanate was added to this solution. The further processing of this mixture was performed as in Example 1. After the solvent, the ester and a small amount of excess cetyl alcohol has been distilled out, a chocolate-brown, solid product is obtained containing 4% vanadium. It is soluble in Decalin or other hydrocarbons, for example.

EXAMPLE 3

3.8 kg of vanadyl acetate was dissolved in a high-boiling hydrocarbon mixture. After the addition of 54.5 kg of stearyl titanate, the mixture was heated with refluxing for two hours, then the solvent as well as the excess stearyl alcohol was distilled out insofar as possible, finally in the vacuum produced by an oil pump. What remained was a solid, chocolate-brown product which, at a titanium content of 4% and a vanadium content of 1.9%, consisted mainly of the desired di(tristearyltitanate)-oxo-vanadate(IV). It, too, is easily soluble in aliphatic hydrocarbons (n-hexane, for example).

0.533 kg of vanadyl (IV) acetate was suspended in a mixture of aliphatic hydrocarbons, having a boiling range between 184 to 211 degree C. To this suspension 2,5 kg of zirconium butylate was added. The resulting mixture was heated up to 135 degree C. and then boiled under reflux during one hour, during this period the vanadyl acetate was dissolved and butyl acetate was formed. The latter was distilled off, whereby the temperature of the sump rose to 185 degree C. The resulting black-greenish solution, containing some solid by-product, was filtered and then the solvent was distilled off at 0,1 mbar by means of a rotary film evaporator. A dark brown product of a tough resenous consistency was obtained containing 22,9% of zirconium and 7,6% of vanadium.

What is claimed is:

1. In a process for the formation of a polymer of a monomer of the group consisting of olefins, dienes, styrene, vinyl chloride, acrylic acid esters and epoxides, wherein the monomer is subjected to polymerization conditions in the presence of a polymerization catalyst therefor, the improvement wherein said polymerization catalyst comprises a compound of tetravalent vanadium of the general formula

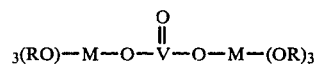

wherein
M represents a metal of the fourth group of the Periodic Table of the Elements and
R represents an alkyl, cycloalkyl or aryl moiety of 1 to 20 carbon atoms.

2. A process according to claim 1, wherein M is titanium.

3. A process according to claim 1, wherein the monomer is an olefin.

4. A process according to claim 1, wherein said monomer is vinyl chloride.

5. A process according to claim 1, wherein R is alkyl.

6. A process according to claim 1, wherein the tetravalent vanadium compound is di(tri-butyltitanate)-oxo-vanadate (IV).

7. A process according to claim 1, wherein said tetravalent vanadium compound is di(triacetyltitanate)-oxo-vanadate (IV).

8. A process according to claim 1, wherein said tetravalent vanadium compound is di(tristearyltitanate)-oxo-vanadate (IV).

* * * * *